United States Patent [19]

Boettner

[11] Patent Number: 4,458,082

[45] Date of Patent: Jul. 3, 1984

[54] METHOD FOR RECOVERING INDICINE-N-OXIDE

[75] Inventor: Fred E. Boettner, Huntingdon Valley, Pa.

[73] Assignee: Polysciences, Inc., Warrington, Pa.

[21] Appl. No.: 410,632

[22] Filed: Aug. 23, 1982

[51] Int. Cl.$^3$ ............................................ C07D 209/96
[52] U.S. Cl. .................................... 548/453; 424/274
[58] Field of Search ................. 548/515, 453; 424/274

[56] References Cited

U.S. PATENT DOCUMENTS 3,705,905  12/1972  Culnenor et al. ................... 548/453
4,353,922  10/1982  Pfister ................................. 424/274

OTHER PUBLICATIONS

Mattocks et al., J. Chem. Soc. 1961 5400.

Primary Examiner—Nicholas S. Rizzo
Attorney, Agent, or Firm—Eidelman, Wolffe & Waldron

[57] ABSTRACT

An improved process for recovering Indicine-N-oxide from plant sources which involves water extracting the plant material, preferably by water buffered at pH 7, followed by adsorbing the Indicine-N-oxide from the extract, after which the Indicine-N-oxide is eluted from the adsorbent in alcoholic solution, then concentrated and purified as heretofore.

Desirably, the adsorbed Indicine-N-oxide is water washed prior to elution so as to remove any water soluble impurities that had been adsorbed from the extract.

A preferred adsorbent is a cross linked polystyrene.

4 Claims, 2 Drawing Figures

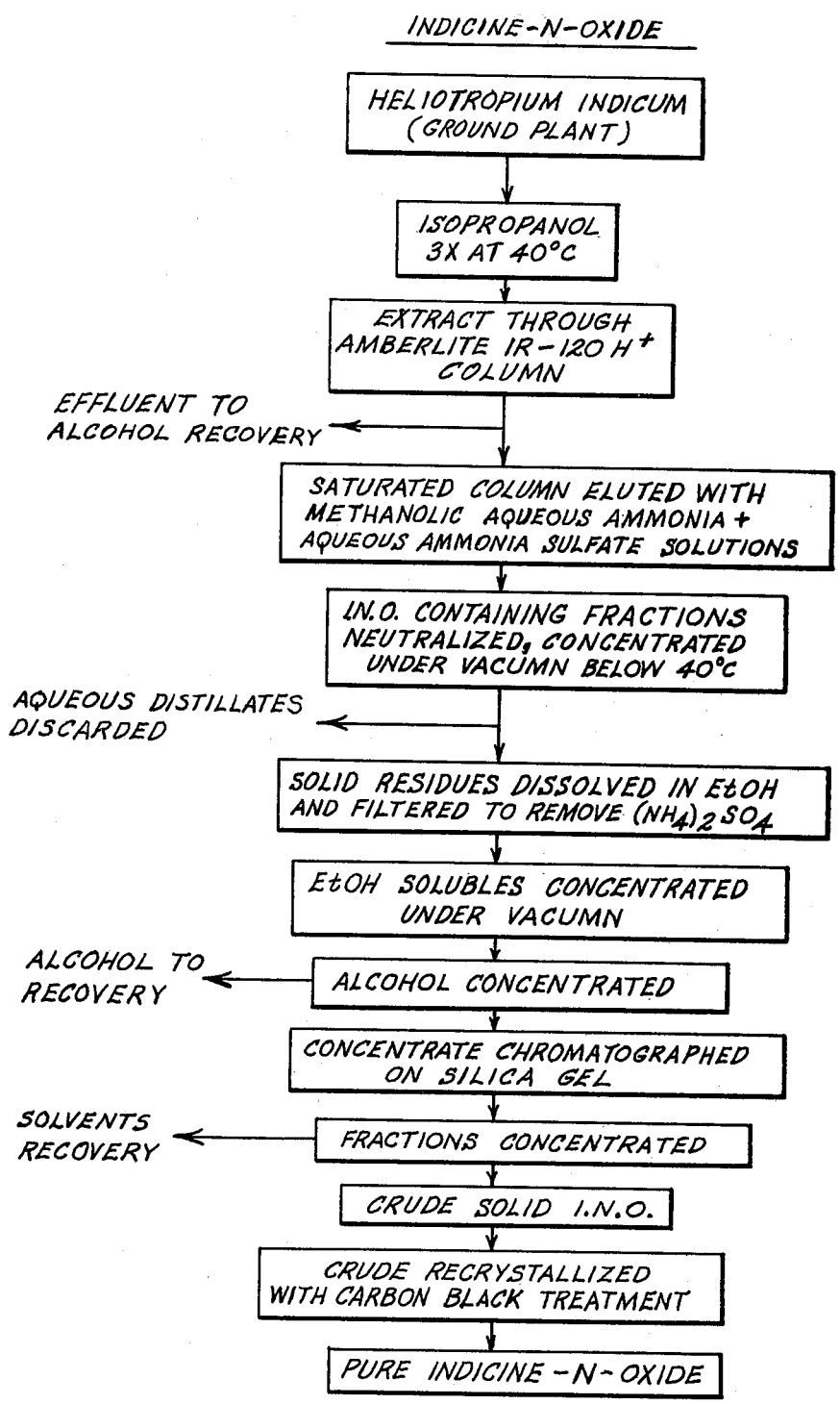

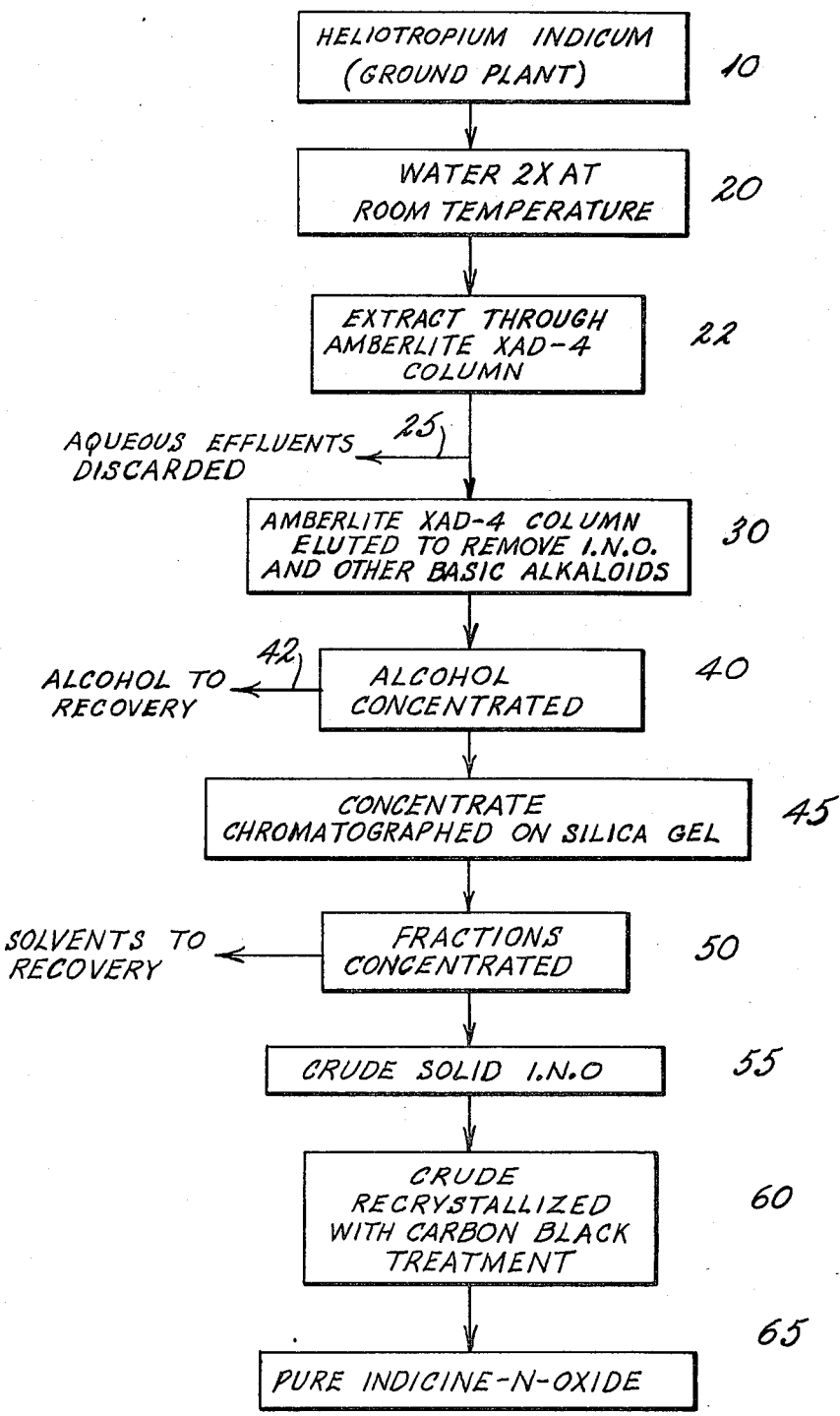

METHOD FOR RECOVERING INDICINE-N-OXIDE

The invention described herein was made in the course of work carried out under Contract No. NO1-CM-07300 with the Department of Health and Human Services.

This invention relates to an improved process for recovering indicine-N-oxide from plant sources.

INTRODUCTION

Indicine-N-oxide, the chemical formula of which is provided below:

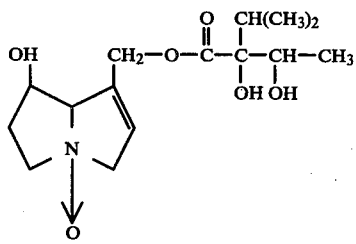

is an anti-cancer agent, reported as being active against several types of leukemia, colon cancer and brain tumors, See, for example:

Latendre, L., et al., *Activity of Indicine-N-oxide in Refractory Acute Leukemia*, Cancer, 47, 437–441, (1981).

Nichols, W. C. Moertel, C. G., Rubin, J., Schutt, A. J. and Britell, J. C., *Phase II Trial of Indicine-N-oxide (INDI) in Patients with Advanced Colorectal Carcinoma*. Cancer Treat. Rep., 65, 337–339, (1981).

Ohnuma, T., Ratner, L. H., Brooks, S. and Holland, J. F., *Initial Clinical Studies with Indicine-N-oxide (NSC 132319)*. Proc. Am. Assoc. Cancer Res., 21, 360, (1980).

Taylor, S., Belt, R., Haas, C., Stephens, R. and Hoogstraten, B., *Phase I Studies of Indicine-N-oxide (IND) in Two Dose Schedules*, Proc. Am. Assoc. Cancer Res., 21, 342 (1980).

The Indicine-N-oxide (hereinafter termed I.N.O.) is obtainable from plant sources, notably from *Heliotropium indicum Linn*, a plant which grows in Brazil, Ghana, Australia and India, wherein the Indicine-N-oxide is present (in the whole plant) as about ½% by weight. Actual assays have ranged from 0.2–0.9%.

It is the object of this invention to provide an improved I.N.O. recovery process.

According to the prior art process (see A. R. Mattocks et al. J. Chem. Soc. 1961, 5400) the I.N.O. may be recovered from the plant sources by extraction of the whole plant with isoproponal followed by treatment of the extract with an acid ion exchange resin e.g., Amberlite 1R-120 H+, to remove the extracted alkaloids from the alcoholic extract solution.

Thereafter, the I.N.O. is eluted from the ion exchange resin by an aqueous solution of methanol, ammonia and ammonium sulfate forming a dilute I.N.O. solution that required neutralization and concentration by evaporating under vacuum and desalting prior to bringing the I.N.O. into an ethanol solution from which purification and recovery are carried out.

Recovery of the I.N.O. by the above described procedure on pilot plant scale, wherein, for example, about one ton batches of plant material is handled, made apparent certain drawbacks in the above described process. In specific, treatment of the aqueous solution resulting from elution of the acid ion exchange resin is cumbersome. The solution must be neutralized, then concentrated under reduced pressure and desalted, all of which is time consuming with large scale batches. Disadvantageously, the I.N.O. tends to decompose on standing in neutral aqueous solutions.

During the course of the efforts which have culminated in the process of the present invention, discovery was made that the time consuming step of evaporating under vacuum conditions could be avoided by adsorbing the I.N.O. from the aqueous eluant, e.g., on a nonionic hydrophobic polymer, as for example, a cross-linked polystyrene bead form polymer. A preferred adsorbent is Amberlite XAD-4, (Rohm & Haas). This approach of treating the aqueous eluant with a polymeric adsorbent adapted to remove the extracted organic materials from aqueous solution allows removal of salts from adsorbent saturated with I.N.O. by water washing of the adsorbent. The I.N.O. could then be eluted from the adsorbent in ethanol, after which recovery of I.N.O. in purified form may be carried out as heretofore.

However, the so-improved process still suffered from a disadvantage in that large amounts of isopropanol are employed to extract a small proportion of I.N.O. from great quantities of plant material, and therefore, an alcohol recovery installation must form part of any large scale system for obtaining I.N.O. from plant sources.

It has now been discovered that I.N.O. can be extracted from the plant source material by water, thereby allowing further improvement and simplification of the process as a whole.

SUMMARY OF THE INVENTION

Briefly stated, the process of this invention employs water extraction of a plant material source of I.N.O., preferably with water buffered to pH 7, then removal of the I.N.O. from the aqueous extract by adsorption thereof on a suitable adsorbent, a preferred bead form adsorbent being a cross-linked polystyrene.

The I.N.O. loaded adsorbent is then water washed to remove water soluble salts therefrom, after which the I.N.O. is eluted from the adsorbent, e.g., with methanol or ethanol, then as heretofore the I.N.O. can be recovered in pure form from alcoholic solution.

DISCUSSION OF THE INVENTION

In the further discussion of this invention, which now follows, reference is made to the attached drawing wherein:

FIG. 1 is a flow sheet illustrating the recovery sequence for I.N.O. according to the already described prior art procedure; and FIG. 2 is a flow sheet illustrating the recovery sequence for I.N.O. according to practice of this invention.

Referring now to FIG. 2 it may be seen that the process of this invention comprises the following steps:

1. Extract the ground *Heliotropium indicum* 10, in extractor 20 (e.g., twice with water at room temperature). Preferably, the water used for extraction contains a pH 7.0 buffer, such as sodium acetate to maintain neutrality.

2. The water extract is passed immediately through adsorber 22, wherein a suitable bead form adsorbent, e.g., Amberlite XAD-4, absorbs the I.N.O. onto the resin bed. The aqueous extract may then be discarded through line 25.

3. After all the water extract has passed through the adsorber 22, e.g., the bed of Amberlite XAD-4, the adsorbent bed is washed with water to remove any water soluble impurities retained by the adsorbent.

4. Elute the I.N.O. from the adsorbent bed column with ethanol or methanol (step 30).

5. Recover the I.N.O., as heretofore, e.g., concentrate the alcoholic extract in evaporator 40, removing the alcohol through line 42 for recovery, and then purify the I.N.O. as usual by HPLC over silica gel at 45 followed by recrystallization 10 to produce pure I.N.O. 65.

As compared to the prior art process illustrated on FIG. 1, many advantages exist, including notably that the present process:

A. Does away with employment of isopropanol (great quantities of) and consequently the equipment to recover this costly raw material for recycle.

B. Does away with the use of a strongly acidic cation exchange column (such as Amberlite IR-120 H+) whereon some of the absorbed I.N.O. decomposes before elution from this column.

Other advantages which exist that may not be immediately apparent from the flow sheets are:

C. The present process affords a purer product, prior to HPLC purification, for not containing basic alkaloids soluble in isopropanol, but, insoluble in water.

D. The total time required for isolation and purification of I.N.O. from a batch of *Heliotropium indicum* is greatly decreased.

E. The cost for isolation of I.N.O. from a batch of *Heliotropium indicum* is greatly reduced (ca 33-50%).

This improvement in product purity (prior to HPLC purification) is attributable to the greater selectivity for I.N.O. present in the process of this invention. Impurities soluble in isopropanol, insoluble in water will remain with the plant residue, and some such impurities are believed to be present in the plant material. Although the full range of possibilities have not been explored as of the date hereof, indications are that the pH of the water extractant is important to the yield and to the initial purity of the I.N.O. Deionized water employed for the extractant results in an extract having pH 9, which level is believed to be not an optimum pH. Preferred is usage of water buffered to pH 7. Sodium acetate is suitable for buffering the water extractant and is preferred.

Another area of the process of this invention wherein possibilities for enhanced selectivity exists is in the nature of the adsorbent. Cross-linked polystyrene (e.g., in bead form) are the most suitable adsorbent substance known as of the date hereof, particularly the proprietary material Amberlite XAD-4. Other polymers suggested for removing organic materials from aqueous solution appear to be less suited to removing I.N.O. from the aqueous extract. Some acrylate polymers tested did not adsorb the I.N.O. at all.

For further understanding of the invention herein the following illustrative examples of the practice thereof are provided.

EXAMPLE 1

A small unknown amount (ca 250 ml.0 of ground *Heliotropium indicum*) was placed in a small beaker and covered with deionized water, then allowed to steep overnight. The next morning the extract was decanted and a Thin Layer Chromatograph (T.L.C.) was run on the extract (the pH of the extract was pH 9.0). This T.L.C. indicated that the water extract contained a fair amount of I.N.O. The water extract was then passed through a ½" diameter × 8" tall column filled with beads of Amberlite XAD-4 (Rohm & Haas). After passage of the extract, the beads in the column were washed with two column volumes of deionized water and then with two column volumes of SDA ethanol. A T.L.C. of all effluents showed that the I.N.O. was present originally in the water extract, then was held up on the Amberlite XAD-4 in the column, then appeared in the ethanol washes. This crude experiment indicated that buffer in the extracting water (adapted to hold the pH of the extract solution at about pH 7.0 should reduce hydrolysis of the I.N.O. It also indicated that the amount of adsorbent beads used in this crude experiment should have been greater.

EXAMPLE 2

In this test 227g (½ pound) of ground *Heliotropium indicum* was placed in a glass 2 liter beaker. This ground plant material was then covered with 1000 ml of deionized water containing 25 g. of sodium acetate (a pH 7.0 buffer). The mixture was stirred well for four hours at room temperature after which the water extract was drained from the plant material and filtered (the pH of the extract solution was pH 7.12; 450 ml of extract solution resulted). The filtrate was then passed through a 2" diameter column containing 875 ml of Amberlite XAD-4 beads. The effluent from the column was tested for I.N.O. leakage (by T.L.C.) when color started from the column effluent and again when all of the water extract had entered the column bed. No I.N.O. leaked from the column.

The wet ground plant material was again mixed with 1000 ml of deionized water containing 25 grams of sodium acetate, stirred well and allowed to steep overnight. In the morning, the water was drained from the plant material and filtered. The filtrate (950 ml, pH 7.3) was checked for I.N.O. content by T.L.C. and then put through the same Amberlite XAD-4 beads in the column. There was no leakage of I.N.O. on passage of this extract solution through the column. A third 1000 ml of deionized water, containing 25 grams of sodium acetate was mixed with the ground plant material stirred well and allowed to steep overnight. In the morning the water extract was drained from the plant material and filtered (1100 ml, pH 6.9). A T.L.C. examination indicated that only a trace of I.N.O. was present in this third extract. This third water extract also was passed through the Amberlite XAD-4 beads in the column. Again, there was no leakage of I.N.O. from the column. The column was then washed with 750 ml of deionized water to remove any trapped salts from the beads. The column was then washed with 1150 ml. of SDA ethanol to remove all adsorbed and absorbed organic materials from the beads. The effluent from this alcohol wash was collected in 250 ml. flasks. A T.L.C. analysis showed that the I.N.O. was in Fractions 3 through 7 and a trace amount of the I.N.O. was present in Fraction 8. Fractions 3 through 8 were combined and concentrated at 40° C. under reduced pressure giving 3.9 grams of a dark brown semi-solid substance. An HPLC analysis of this concentrate showed that according to the water extraction the *Heliotropium indicum* contained 0.436% I.N.O. in the plant material. A previously run assay of the same batch of *Heliotropium indicum* using isopropanol for extraction and the ion exchange adsorption technique had shown 0.548% I.N.O. These results are believed to be comparable, as within expected experimental error.

EXAMPLE 3

A 2000 gallon stainless steel tank having a bottom drain is fitted for use as an extractor as follows:

Connect the bottom drain to a Waukesha stainless steel pump by means of 1" S.S. (stainless steel) pipe using "Triclover" fittings. Connect the outlet of the pump using 1" pipe to a 1" tee. Connect the other outlets of the tee to 1" ball valves. Connect one of the ball valves to a pipe leading to the top of the kettle. Connect the other ball valve to the top of a 10 "×12' S.S. column containing 5 cu.ft. of washed Amberlite XAD-4. For convenience, the pump should be controllable by means of a float switch in the top of the adsorbent containing column. Place a stainless steel support screen ($\frac{1}{2}$" screen) over the bottom drain inside the kettle. Over this screen place four to six layers of burlap cloth and cover same with a circular piece of 80 mesh S.S. screen to act as a filter.

Place about 3500 lbs of ground *Heliotripoium indicium* in the 2000 gal kettle. Cover this ground plant material with ca. 1500 gals of deionized water containing 250 lbs of sodium acetate dissolved therein. After all of the water solution is in the kettle, open the bottom drain valve and turn on the Waukesha pump, to pump the extract back to the top of the kettle. Percolate the extract solution in this manner for 24 hours. At the end of this time period, arrange the valves above the pump so that the aqueous extract is pumped to the adsorbent column on demand of the float switch at the top of the column. Open the bottom drain of the XAD4 column so that the flow rate through the column does not exceed 10 gals/min (preferably about 3-4 gal/min). The effluent from this column is discarded to the drain as long as it does not contain any indicine-N-oxide (as shown by a T.L.C. test specific for N-oxides). Continue pumping the first water extract through the Amberlite XAD-4 column until the pump can no longer maintain a head in the column indicating, thereby, that all of the first extract has drained from the plant material (about 4-5 hours). Then switch the valve off the column and pump another 950-1000 gal of deionized water, containing 250 lbs of sodium acetate into the kettle. Percolate this solution through the ground *Heliotropium indicum* for 24 hours as previously. At the end of this time period pump this second extract through the Amberlite XAD-4 column as previously (about 6-8 hours). When all of the second extract is through the Amberlite XAD-4 column wash the column with deionized water until the effluent is clear and colorless (about four column volumes, i.e., 190-200 gals).

After the Amberlite XAD-4 in the column has been washed with water, rearrange the pump and float switch so that four column volumes (190-200 gals) of 95% ethanol can be pumped through the column at a rate of ca. 2-3 gals/min. The effluent from this column should be checked for indicine-N-oxide by T.L.C. every ten gallons. When all of the indicine-N-oxide has been eluted from the Amberlite XAD-4 in the column, stop. The ethanolic eluant which now contains the indicine-N-oxide is then concentrated almost to dryness under reduced pressure at 40° C. giving about 12 to 13 Kg of an amber colored semi-solid crude product.

This amber colored semi-solid is then chromatographed on silica gel as follows:

Slurry pack two 6"×10' S.S. columns with 135 lbs of chromatographic grade silica gel (Davisil 633) using methylene dichloride as the liquid phase. Dissolve 6-6.5 Kg of the amber colored semi-solid in 4.5 gal of methylene dichloride (MDC) and one gal of methanol (MeOH). Pump the solution into the first of the two silica gel columns connected in series and chromatograph using a step gradient of the following solvents by volume:

| Step | Solvent Mix | Amount |
|---|---|---|
| 1 | MDC:MeOH:$H_2O$ = 89:10:1 | 215 gal |
| 2 | MDC:MeOH:$H_2O$ = 82:16:2 | 191 |
| 3 | MDC:MeOH:$H_2O$ = 77:20:3 | 183 |
| 4 | MDC:MeOH:$H_2O$ = 72:24:4 | 60 |

Pump these solutions through the columns at the rate of 7-10 gals/hour at a pressure of 150-190 psi. Collect the samples in 5 gal pails after the indicine-N-oxide begins coming off the columns (as shown by T.L.C.). Combine like fractions (as shown by T.L.C.) and concentrate them to dryness. Dissolve the concentrate in an equal weight of anhydrous ethanol, treat the solution with carbon black and filter, dilute the filtrate with about 6 to 8 volumes of dry acetone with good stirring to cause the indicine-N-oxide to crystallize.

Chromatograph the remainder of the semi-solid concentrate from the Amberlite XAD-4 column as described above, to obtain the rest of the indicine-N-oxide in crystal form.

Combine the total amount of the crystalline indicine-N-oxide from the two chromatograms and again recrystallize as above to obtain 7.28 Kg. of pure crystalline indicine-N-oxide.

I claim:

1. In a process of recovering indicine-N-oxide from *Heliotropium indicum*, the improvement which comprises water extracting the plant material thereby extracting the indicine-N-oxide in aqueous solution, then adsorbing the indicine-N-oxide from the aqueous extract, whereafter the indicine-N-oxide is eluted from the adsorbent.

2. The process of claim 1 including water extracting with buffered water at about pH 7.

3. The process of claim 1 including water washing the adsorbed indicine-N-oxide to remove water soluble impurities from the adsorbent prior to elution of the indicine-N-oxide from the adsorbent.

4. The process of claim 1 including adsorbing the indicine-N-oxide on a cross-linked polystyrene.

* * * * *